United States Patent [19]

Hellergvist

[11] Patent Number: 5,010,062

[45] Date of Patent: Apr. 23, 1991

[54] THERAPEUTIC AGENT AND METHOD OF INHIBITING VASCULARIZATION OF TUMORS

[75] Inventor: Carl G. Hellergvist, Brentwood, Tenn.

[73] Assignee: Vanderbilt University, Nashville, Tenn.

[21] Appl. No.: 411,674

[22] Filed: Sep. 25, 1989

[51] Int. Cl.$^5$ .................... A61K 37/02; A61K 39/085
[52] U.S. Cl. ...................................... 514/54; 514/908; 536/55.1
[58] Field of Search .................. 514/54, 908; 536/55.1

[56] References Cited

U.S. PATENT DOCUMENTS

| | | | |
|---|---|---|---|
| 4,522,803 | 6/1985 | Lenk et al. | 436/829 |
| 4,882,317 | 11/1989 | Marburg et al. | 536/55.1 |
| 4,895,838 | 1/1990 | McCluer et al. | 514/54 |
| 4,939,083 | 7/1990 | Fukuda et al. | 536/55.1 |
| 4,950,750 | 8/1990 | Ogawa et al. | 536/55.1 |

*Primary Examiner*—Ronald W. Griffin
*Attorney, Agent, or Firm*—Tilton, Fallon Lungmus & Chestnut

[57] ABSTRACT

A method for at least partially inhibiting vascularization of a developing solid tumor. Said method comprising parenterally administering to the patient the polysaccharide toxin produced by group B β-hemolytic Streptococcus bacteria known as GBS toxin in an amount effective for said

THERAPEUTIC AGENT AND METHOD OF INHIBITING VASCULARIZATION OF TUMORS

FIELD OF INVENTION

The field of this invention is therapeutic agents and methods of treating tumors.

BACKGROUND OF INVENTION

Group β-hemolytic Streptococcus (GBS) are ubiquitous microorganisms. GBS is not known to cause any harmful infections in humans except for very young babies. GBS pneumonia, also called "early-onset disease", is associated with high morbidity and mortality in newborn infants. The GBS infection may be present on the day of birth and is particularly frequent in premature babies. After the infants reach a few weeks of age and normal lung development has occurred, they are no longer subject to GBS pneumonia.

In a series of studies conducted by Dr. Carl G. Hellerqvist and his associates at the Vanderbilt University School of Medicine, Nashville, Tennessee, a polysaccharide GBS toxin was identified. This toxin, which is elaborated by Group B β-hemolytic Streptococcus is believed to be a major factor in the complications of GBS pneumonia.

The GBS toxin has been isolated from GBS culture media, purified, and partially characterized. See Hellerqvist, et al. (1981), *Pediatr.Res.*, 15:892-898; Rojas, et al. (1981), *Pediatr.Res.*, 15:899-904; Rojas, et al. (1983), *Pediatr. Res.*, 17:1002-1008; and Hellerqvist, et al. (1987), *Proc. Natl. Acad. Sci. USA*, 84:51-55. In these studies, sheep were used as an experimental model for testing the effect of the GBS polysaccharide toxin on lungs. Differing from human, the lungs of mature sheep as well as young sheep are subject to GBS toxin. When the toxin is infused into sheep it produces pulmonary hypertension and increased pulmonary vascular permeability. These changes are similar to those occurring in newborn infants with Group B streptococcal sepsis.

GBS toxin is a complex polysaccharide with an estimated molecular weight of around 200,000. This polysaccharide shares immunological structural features with the group antigen as reported in Hellerqvist et al. (1981), cited above, and contains phosphodiester structures deemed essential directly or indirectly to toxin function [Hellerqvist, et al. (1987), cited above.]

SUMMARY OF INVENTION

This invention is based on the novel concept that GBS toxin can be used as a therapeutic agent in combating tumors through inhibition of vascularization. To grow beyond about 1 cubic centimeter in size, solid tumors must vascularize, inducing the formation of new blood vessels for supplying the tumor as it enlarges. Underlying the invention is the recognition that the newly forming vasculature is in a developmental state comparable to the embryonic lung vasculature of premature infants and neonates at time of birth. The cells of the vasculature of such tumors are in a receptive state for interacting with GBS toxin. Specifically, it is believed that the lung cells of the vasculature of the tumor, being embryonic genetically, have cellular receptors for the critical structural sites of GBS toxin. Such receptors will permit toxin to interact with the vasculature of the tumor body and thereby inhibit tumor vascularization by inducing a host mediated destruction of the newly formed capillaries. This interaction will be specific to the tumor site's vasculature. Mature normal vasculature, such as lung vasculature, no longer have receptors which interact with the GBS toxin. Further, the toxin will be systemically safe for administration to a patient by intravenous infusion. GBS and the toxin which it produces are known to be tolerated by normal adult humans, although GBS infections in adults may be associated with other complications, such as diabetes mellitus, hepatic failure, and certain forms of malignancy [*Archives Internal Medicine* (1988), 145, 641-645.]

The method of this invention was originally demonstrated with respect to lung tumors. However, it is believed to be generally applicable to solid tumors which are developing new capillaries to supply blood to the tumor. In particular, it is believed that the method will be particularly effective for carcinomas and adenocarcinomas. The objective of the method is to at least partially inhibit the development of the vasculature of the solid tumor, carcinoma, adenocarcinoma, or lung tumor. Inhibition of the development of new capillaries for supplying blood to the developing tumor tend to arrest the growth of the tumor, and should be of assistance in controlling or eradicating solid tumors.

DETAILED DESCRIPTION

This invention utilizes a polysaccharide toxin produced by Group B β-hemolytic Streptococcus bacteria as a therapeutic agent for treatment of developing solid tumors in human patients. This toxin, referred to herein as GBS toxin, is used in purified form, which consists of a complex polysaccharide polymer with mannosyl phosphodiester groups, as described by Hellerqvist, et al. (1987), *Proc. Natl. Acad. Sci. USA* 84:51-55. For purpose of inhibiting the vascularization of a developing tumor, GBS toxin can be parenterally administered in an amount effective for the inhibition. For example, the toxin can be intravenously infused in an aqueous solution in doses of from 1 to 10 micrograms (mcg) per kilogram (kg) of patient body weight. More specifically, the administration vehicle may comprise sterile normal saline, and may contain the toxin in amounts of 0.5 to 2 milligrams (mg) per 30 milliliters (ml) of solution. The treatment protocol can be varied as required for the most effective results. For example, administration of the toxin may be repeated as required, viz. on a weekly basis.

Dose size and the progress of the GBS toxin can be determined by monitoring the number of circulating granulocytes. As the toxin interacts with the receptors of the developing tumor vasculature, the circulating granulocytes will be affected. Treatment protocol will vary with the kind of solid tumor being treated. On the basis of present evidence, the method is potentially applicable to solid tumors throughout the human body, especially to tumors classified as carcinomas or adenocarcinomas. The degree of effectiveness will depend on the extent to which the developing vasculature of the tumor provides receptors for the GBS toxin. The vasculature of lung tumors has been found to possess such receptors. Further, assays on human large and small cell carcinomas demonstrated GBS toxin binding sites in the vasculature of these tumor masses. Also, human large cell adenocarcinoma used in mouse studies leading to this invention were immunologically identified by monospecific antibodies to human breast adenocarcinomas. Although not yet demonstrated with certainty, it is believed that the vasculatures of developing solid tumors, in general, provide at least some GBS toxin binding sites, and the method of this invention can therefore be used for obtaining at least partial inhibition of further vasculature development.

It is expected that the toxin receptor interaction with developing capillaries in the tumor will lead to granulocytopenia and subsequent release of the enzyme elastase from the granulocytes. The reduced presence of elastase may be monitored by radioimmunoassay, which can serve as another means of monitoring the treatment. In addition, oxidative damage induced by the granulocytes can be monitored by measuring conjugated dienes in the plasma.

GBS toxin for use in the method of this invention can be obtained by culturing strains of Group B $\beta$-hemolytic Streptococcus which have recently infected or are capable of infecting newborn infants. Isolates of such strains can therefore be obtained from the blood of infants infected and symptomatic with GBS pneumonia. Strains of GBS which have been maintained by successive in vitro culturing would not be suitable as a source of the GBS toxin. Carbohydrate elaborated in the culture medium may be deficient in the specific structural features, assumed to be phosphodiester residues which interact with the receptors of embryonic lung cells. The suitability of the polysaccharide component can be determined by testing in sheep, as described by Hellerqvist, et al. (1981), *Pediatr. Res.* 15:892-898; and Rojas, et al. (1981), *Pediatr. Res.* 15:899-904. Action of the toxin on sheep lungs is to increase pulmonary hypertension, manifested by increased pulmonary artery pressure and also by increased lung vascular permeability.

The receptor interaction capability of the GBS toxin can be enhanced by in vivo passage of a GBS strain. For example, mice or rabbits may be inoculated by intraperitoneal injection. After the mice or rabbits have become seriously ill, they are sacrificed, their spleens excised, and the GBS culture recovered from the spleens used for infection in the next mouse or rabbit. Multiple in vivo passages are desirable, such as, for example, five passages through mice. This procedure is described in detail by Hellerqvist, et al. (1987), cited above.

Using a GBS strain producing a highly interacting form of the GBS toxin, the strain can be cultured on a larger scale in vitro to elaborate the GBS toxin in the culture medium. Details of the procedure for carrying out such culturing are also described in Hellerqvist, et al. (1987), cited above. For example, as described by Hellerqvist, et al. (1981), cited above, the GBS strain may be cultured in a Todd Hewitt Broth using an 18 hour incubation at 35° C. The initial culturing can be used to produce inoculum for larger batches, which can be carried out in Todd Hewitt Broth, incubating for 24-48 hours at 25° to 37° C. with the inoculated flask in a gyratory shaker.

After the culturing of the GBS, the cells are separated from the supernatant, which contains the GBS toxin. Suitable recovery procedures are described in Hellerqvist, et al. (1981, 1987), cited above. Briefly, after the culture supernatants have been autoclaved, ethanol is added to a 70% concentration. The resulting precipitate may be subjected to an aqueous phenol extraction, following the procedure described by Galanos, et al. (1969), *Eur. J. Biochem.*, 9:245-249. For example, as described by Hellerqvist, et al. (1981), cited above, the extraction may be carried out with an extracting solvent composed of equal parts of water and phenol which is applied to the ethanol precipitate at an elevated temperature, such as with slow heating for 30 minutes up to 70° C. The water phase of the extraction can be dialyzed against water and purified by gel filtration, as described by Hellerqvist, et al. (1987), cited above. Alternatively, GBS toxin in a high molecular weight form (Hellerqvist, et al., 1981, cited above) is recovered from the attached precipitate by chromatography procedures (Hellerqvist, et al., 1981, cited above), omitting the phenol water extraction procedure. GBS toxin may also be obtained after protease digestion of bacterial membrane fractions (Hellerqvist, et al., unpublished).

The potency of isolated GBS toxin as a tumor growth inhibitor may be ascertained by peroxidase-antiperoxidase (PAP) assays of tumor tissue specimens using anti-GBS toxin IgG, and by infusion in a sheep model at 2 ugs $10^{-11}$ moles per kg (Hellerqvist, et al., 1981, 1987, cited above). For the purposes of this invention, the term GBS toxin means any purified fraction or component of the natural GBS toxin, or derived from media or protease digests of lysed GBS bacterial, and whose toxicity can be confirmed by either of the specified assay procedures.

GBS toxin can be fractionated on lentil lectin. The most potent GBS toxin fraction passes through two serially mounted lentil lectin columns. A GBS toxin fraction of lower specific toxin activity in the sheep model (see dose response FIG. 3. Hellerqvist, et al., 1971) can be eluted from the lentil lectin columns with a-methylmannoside. This indicates an increased level of substitution with mannosyl-phosphate groups increases toxic potency but decreases the lentil lectin affinity. The most potent form of the toxin has an estimated molecular weight of approximately 200,000, and is apparently composed of rhamnose, mannose, glactose, glucose, N-acetyl-glucosamine, and N-acetyl galactosamine in an approximate molar ratio of 2:2:3:1:2:1, respectively.

The method is further illustrated by the following experimental examples.

EXAMPLE I

Purified GBS toxin was prepared according to the following procedures.

Isolation of GBS Toxin

Growth of Bacteria. Todd Hewitt broth (THB) 10 ml is inoculated with a frozen stock culture, established from isolates from diseased neonates and incubated 9-12 h. The so-obtained cultures are used as inocula in the below-described procedures aimed at obtaining cultures with elevated plasmid content and GBS toxin production capabilities.

Procedure 1. A mouse is injected aseptically in the peritoneal cavity with 1 ml of the culture. Hellerqvist, et al. (1987). When septicemic, the animal is sacrificed and the spleen removed. A Sheep Blood Agar (SBA) plate is "contaminated" with the spleen and the plate streaked with a loop to obtain single colonies. The spleen will be placed in 10 ml of Todd Hewitt broth and this culture will be used for the second mouse passage, provided the SBA plate shown no other colony than $\beta$-hemolytic Streptococci. By the fifth passage and any passage thereafter, 15 l batches of Todd Hewitt broth are inoculated with $10^9$ bacteria from the spleen cultures and inoculated at 37° C. on a gyratory shaker for 42 h.

Procedure 2. THB, supplemented with serum, from human or other species, is inoculated and the resulting culture is used in a serial passage as a substitute for the mouse passage sequence. By the fifth or more subculture the bacteria are grown in large batches in THB or THB supplemented with serum and glucose.

Quality Control. Aliquots are withdrawn from each flask after completion of the incubation and used to inoculate plates with:

(a) Sabaraud Dextrose Agar (SDA) in duplicate,
(b) Eosin Methylene Blue (EMB),
(c) Trypticase Soy Agar (TSA), and
(d) SBA.

The flasks are autoclaved and stored at 4° C. for 38 h, which will be sufficient time for all plates to show absence of:

(1) yeasts and fungi on the SDA plates, one incubated at 37° and one at room temperature,
(2) gram-negative contamination on the EMB plate.

Identical set of plates and sterility standards are used to assure that no microbia growth whatsoever occurs on chromatography column beds or in dialysis bags during the purification procedures.

THB Media Preparation. THB media is used supplemented with serum and glucose 2 g/l. To circumvent problems with manufacturers adding or not adding yeast extract to the media lots without a record, media batches can be filtered through a 10,000 Mw cut off filter cassette (Millipore Corp.). If unfiltered media is used possible yeast mananas will have to be removed by most readily lectin chromatography.

Isolation of GBS Toxin. The procedures followed are our original procedures (Hellerqvist, et al., 1981, Pediatr. Res. 15:892-898). Autoclaved culture supernatants or membrane protease digests determined free of any microbial contamination are precipitated by being made 70% in ethanol and subjected twice to phenol water extraction Gallanose, et al. (1969). The water phase is collected for dialysis against water and subjected to subsequent DE52 chromatography. GBS toxin in water binds to DE52 and is eluted at approximately 0.25 M NaCl when a gradient from 0 to 0.4 M NaCl is applied Hellerqvist, et al. (1987). Fractions are monitored by optical rotation and a phenol sulfuric calorimetric assay. Next, gel filtration on Sephacel S-300 yields GBS toxin, which elutes slightly included on the column. After dialysis and lyophilization, GBS toxin is subfractionated on Lentil lectin affinity column developed in phosphate buffered saline (PBS). GBS toxin (2-5 mg) off the Sephacel column is dissolved in PBS (0.5 ml) and applied to a Lentil lectin column (1x5 cm). The material not retained on the column (GBS toxin LL) eluting in two column volumes is dialyzed and lyophilized and reapplied to the regenerated Lentil lectin column. The flow through peak is collected as GBS toxin LL1 and a partially retained fraction eluting within 1.5 column volumes as GBS toxin LL2. This procedure is necessary if unfiltered THB media is used, since yeast mananas could contaminate the preparation.

It is recommended the prefiltered THB is used. The reason for the recommendation is that GBS toxin itself has structural features with sufficient affinity for Lentil lectin to require elution with a-methyl-mannoside. These GBS toxin fractions, however, show less specific activity when infused in the sheep model than either GBS toxin LL1 or LL2.

Characterization of GBS Toxin LL1 and LL2. GBS toxin LL1 and LL2 are the most potent pathophysiological response modifiers isolated, and exhibit activity at 1/60 the original dose, or $10^{11}$ moles per kg in the sheep model dose have virtually identical $^{1}H$NMR spectra which contains signals characteristic of a polysaccharide also containing phosphodiester residues Hellerqvist, et al. (1987). Subjected to sugar analysis the polysaccharide constituting this most potent GBS toxin yields the composition shown in Table 1.

TABLE 1

| Sugar Compositions of GBS Toxin LL1 and LL2 | |
|---|---|
| Sugar | Mol % |
| rhamnose | 11.3 |
| mannose | 13.6 |
| glactose | 17.7 |
| glucose | 13.1 |
| N-acetyl-glucosaine | 29.5 |
| N-acetyl-galactosamine | 9.7 |

EXAMPLE II

The effect of GBS toxin prepared as described in Example I was studied with respect to the growth rate of human large cell adenocarcinoma propagated in nude mice. The purified fraction of the GBS toxin LL1 was used, which had been prepared as described in Example I.

EXPERIMENTAL

Tissue Source. A human lung large cell adenocarcinoma (BRX Lu 4), with a relative DNA index of 1.4 was established in tissue culture grown in RPMI 1640 supplemented with 10% fetal calf serum. The cells in culture were colonogenic in soft agar, and retained a relative DNA index of 1.4. Immunocytochemical characterization showed positive for cytokeratin and cross-reaction with 2 of 2 monoclonal antibodies directed against large cell breast adenocarcinoma of breast origin.

Tissue Inoculum. Tumor inocula were prepared from cells grown on tissue culture dishes to 90 percent confluency. $10^7$ cells suspended in phosphate buffered saline (PBS) were injected from individual syringes, subcutaneously via ventral route in each of 22 nude mice. After 10 days average tumor size reached 100+ 12 cubic millimeters (cmm) and the animals were divided into three groups of 7, 7, and 8 individuals with randomized size tumors. A fourth group of 7 non tumor bearing animals served as control group.

GBS Toxin Inoculum. Inoculum were prepared by dissolving the polysaccharide toxin [fraction L1) in PBS in concentrations to give inocula of 2 ug/kg and 20 ug/kg corresponding to 0.25 and 2.5 picomole per injection, respectively. Dextran 70 (Pharmacia, Uppsala, Sweden) at 20 ug/kg or 7 picomole per injection was used as control.

Injection regiment. Mice in four groups, Groups 1-3 tumor bearing and 4 non-tumor bearing were injected intravenously through tailveins with 100 ul of PBS containing: 2.5 picomoles GBS toxin Group 1 and Group 4; 0.25 picomoles GBS toxin Group 2, and 7 picomoles of Dextran Group 3. Injections were Monday, Wednesday, and Friday, and tumor volumes were calculated from height, width, and length measurements each day of injection.

RESULTS

Group 4 demonstrated that GBS toxin at 20 ug/kg had no effect on weight gain and the animals showed no signs of toxicity. Doses of 4 mg/kg were used previously Hellerqvist, et al. (1981) in lead sensitized animals with no apparent effect. Preliminary histological examination revealed no apparent tissue damage in either of lung, liver, kidney, spleen or brain. Tumor growth in the different Groups occurred at different rates. A preliminary examination of the tumors at the time of termination of the animals showed that necrosis and hemorrhage affected more than half of the tumor mass in 6 of the 7 animals in Group 1, receiving 20 ug/kg of GBS toxin. No such damage was apparent in the Group receiving Dextran at the equimolar concentration. The group receiving 2 ug/kg showed an intermediary histological picture.

Data obtained showed that GBS toxin reduced equally efficiently the growth rate of the tumors over the first 6 days of treatment and that over the following 8 days the rate of growth in Group 1 remained at the slower rate, whereas the rate in Group 2 was elevated towards the rate seen in Group 3 receiving Dextran. At the termination of the experiment average tumor sizes+standard deviations of the means were:

| | |
|---|---|
| Group 1, receiving 2.5 picomoles GBS toxin/inj $p < 0.005$ | 422 + 68 |
| Group 2, receiving .25 picomoles GBX toxin/inj $p < 0.05$ | 550 + 71 |
| Group 3, receiving 7.0 picomoles Dextran/inj | 731 + 132 |

No significant changes in weight gain were observed between tumor bearing and non tumor bearing mice receiving 2.5 picomole GBS toxin/inj or between any of the groups.

DISCUSSION

This data demonstrates that GBS toxin alone reduces the rate of growth in a dose dependent way of the human tumor cells by approximately 45% over Dextran at a dose of 20 micrograms or 2.5 picomoles per kg and by 25% at a dose of 2 microgram or 0.25 picomoles per injection. GBS toxin at 1 ug/kg induces severe respiratory distress in the sheep model and this is assumed to be due to the total inflammatory and immunologic response involving macrophages B and T lymphocytes and granulocytes. The selected mouse model lacks T cells and thus also the T cell dependent B cell response and thus demonstrates the value of GBS toxin as an agent active as a tumor growth suppressor presumably through its action on capillary endothelium. It is postulated that in the tumor bearing normal individual this action would lead to vessel destruction and subsequent tumor necrosis. The histochemical studies done with GBS toxin and anti GBS toxin-IgG and control IgG with sheep lung and human tumor tissues corroborates this assumption.

The fact that GBS toxin shows specific binding to the capillaries of different human tumor tissues and reduces the growth rate in the exponential phase of a human tumor in an immunodeficient animal model, by induction of a pathophysiology similar to what is seen in sheep lung and human neonatal lung affected by GBS toxin or early onset disease respectively, suggests that GBS toxin will inhibit the vascularization of human tumors and thereby their growth.

I claim:

1. The method of at least partially inhibiting vascularization of a developing solid tumor in a human patient, comprising parenterally administering to the patient the polysaccharide toxin produced by group B $\beta$-hemolytic Streptococcus bacteria known as GBS toxin, said GBS toxin being in a purified, toxin-active form and being administered in an amount effective for said inhibition.

2. The method of claim 1 in which said tumor is a carcinoma associated with and dependent on vascularization.

3. The method of claim 1 in which said tumor is an adenocarcinoma associated with and dependent on vascularization.

4. The method of claim 1 or claim 2 in which said GBS toxin is parenterally administered by intravenously infusing an aqueous solution of the toxin.

5. The method of claim 1 or claim 2 in which said GBS toxin is parenterally administered in a dose amount corresponding to 1 to 10 micrograms (mcg) of said toxin per kilogram (kg) of body weight of said patient.

6. The method of claim 1 in which said tumor is a lung tumor with a developing vasculature.

7. The method of inhibiting vascularization of a vasculature dependent developing carcinoma or adenocarcinoma, comprising intravenously infusing the patient with an aqueous solution of the polysaccharide toxin produced by Group B $\beta$-hemolytic Streptococcus bacteria known as GBS toxin, said GBS toxin being in a purified, toxin-active form and being administered in an effective dose amount of from 1 to 10 micrograms (mcg) of said toxin per kilogram (kg) of body weight of said patient.

8. The method of inhibiting vascularization of a developing lung tumor, comprising intravenously infusing the patient with an aqueous solution of the polysaccharide toxin produced by Group B $\beta$-hemolytic Streptococcus bacteria known as GBS toxin, said GBS toxin being in a purified, toxin-active form and being administered in an effective dose amount of from 1 to 10 micrograms (mcg) of said toxin per kilogram (kg) of body weight of said patient.

* * * * *

UNITED STATES PATENT AND TRADEMARK OFFICE
CERTIFICATE OF CORRECTION

PATENT NO. : 5,010,062

DATED : April 23, 1991

INVENTOR(S) : Carl G. Hellerqvist

It is certified that error appears in the above-identified patent and that said Letters Patent is hereby corrected as shown below:

On the title page, under item [19], and in item [75]:

Please correct inventor's name "Hellergvist" to read -- Hellerqvist--.

Signed and Sealed this

Fifth Day of January, 1993

Attest:

DOUGLAS B. COMER

Attesting Officer

Acting Commissioner of Patents and Trademarks